United States Patent
Kovi et al.

(10) Patent No.: US 11,654,151 B2
(45) Date of Patent: May 23, 2023

(54) STORAGE-STABLE READY-TO-USE FORMULATIONS OF TIGECYCLINE

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Sanjaysinh Fatesinh Thakor, Vadodara (IN); Rahul Dixit, Indore (IN)

(73) Assignee: RK PHARMA INC., Pearl River, NY (US)

( * ) Notice: Subject to any disclaimer, the term of this patent is extended or adjusted under 35 U.S.C. 154(b) by 201 days.

(21) Appl. No.: 17/075,734

(22) Filed: Oct. 21, 2020

(65) Prior Publication Data
US 2021/0205336 A1    Jul. 8, 2021

(51) Int. Cl.
| | | |
|---|---|---|
| A61K 31/65 | (2006.01) | |
| A61K 47/52 | (2017.01) | |
| A61K 47/18 | (2017.01) | |
| A61K 9/08  | (2006.01) | |
| A61K 47/02 | (2006.01) | |

(52) U.S. Cl.
CPC ............... *A61K 31/65* (2013.01); *A61K 9/08* (2013.01); *A61K 47/02* (2013.01); *A61K 47/183* (2013.01); *A61K 47/52* (2017.08)

(58) Field of Classification Search
CPC ...... A61K 31/65; A61K 47/02; A61K 47/183; A61K 47/26; A61K 47/52; A61K 9/0019; A61K 9/08; A61K 9/10; A61K 9/107
See application file for complete search history.

(56) References Cited

U.S. PATENT DOCUMENTS

2009/0275660 A1* 11/2009 Chauhan ............... A61K 9/19
                                                    514/616
2015/0190511 A1*  7/2015 Qin ....................... A61K 47/02
                                                    514/153

* cited by examiner

*Primary Examiner* — Savitha M Rao
(74) *Attorney, Agent, or Firm* — Antonio Papageorgiou

(57) ABSTRACT

Liquid parenteral formulations are provided that include tigecycline and at least one or more pharmaceutically acceptable excipient or adjuvant, where the formulation is ready to use without additional steps for reconstitution at the time of administration.

3 Claims, No Drawings

STORAGE-STABLE READY-TO-USE FORMULATIONS OF TIGECYCLINE

BACKGROUND

The present application relates to a stable, ready to use, tigecycline injectable formulation.

Tigecycline, also known as (4S,4aS,5aR,12aS)-9-[2-(tert-butylamino)acetamido]4,7-bis(dimethylamino)-1,4,4a,5,5a,6,11,12a-octahydro-3,10,12,12a-tetrahydroxy-1,11dioxo-2-naphthacenecarboxamide Tigecycline is a tetracycline class antibacterial drug for intravenous infusion. Tigecycline has the molecular formula $C_{29}H_{39}N_5O_8$, and a molecular weight of 585.65. Structure of Tigecycline is depicted in Table A below.

TABLE A

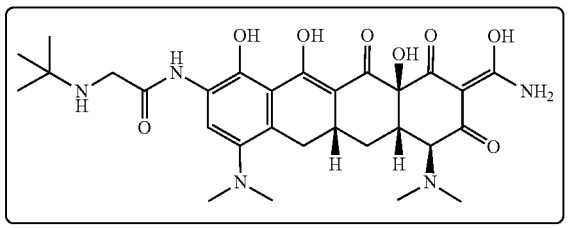 [SMILES: CN(C)c1cc(NC(=O)CNC(C)(C)C)c(O)c2c1C[C@H]1C[C@H]3[C@H](N(C)C)C(=O)/C(=C(\N)O)C(=O)[C@@]3(O)C(=O)C1=C2O]

Tygacil® is an orange lyophilized powder or cake. Each Tygacil® single-dose 5 mL or 10 mL vial contains 50 mg tigecycline lyophilized powder for reconstitution for intravenous infusion and 100 mg of lactose monohydrate. The pH is adjusted with hydrochloric acid, and if necessary sodium hydroxide. The product does not contain preservatives.

Different formulations are also available for Tigecycline. Formulation for tigecycline for injection, USP is an orange lyophilized powder or cake. Each tigecycline single dose 10 mL vial contains 50 mg tigecycline and 82.6 mg of arginine as lyophilized powder for reconstitution for intravenous infusion. The pH is adjusted with hydrochloric acid, and if necessary sodium hydroxide. The product does not contain preservatives.

The commercial formulation of injectable tigecycline is supplied in a single-dose 5 mL glass vial or 10 mL glass vial, each containing 50 mg tigecycline lyophilized powder for reconstitution.

Tygacil® injectable tigecycline also requires an additional step of reconstitution prior to administration. Improper reconstitution may sometimes result in failure to provide a clear solution.

The currently available dosage form of tigecycline for injection is therefore costly to manufacture, distribute and store and inconvenient to use because it is not in a ready-to-use formulation. Therefore, an aqueous and ready-to-use tigecycline solution formulation is highly desirable, reducing manufacturing costs by eliminating the need for lyophilisation and reducing pharmacy time, labour and equipment costs by eliminating the need to reconstitute the dry powder with subsequent further dilution.

SUMMARY

The present application provides a stable, ready-to-use injectable tigecycline solution in infusion bag and a vial, which is easy to administer without need of any reconstitution step and has a desirable solubility, stability and safety profile.

In one or more embodiments there is provided a ready-to-use liquid parenteral formulation of tigecycline in infusion bag.

In still further embodiments provided are ready-to-use liquid parenteral formulations including tigecycline and at least one or more pharmaceutically acceptable excipient or adjuvant in infusion bag.

In another embodiments there is provided a ready-to-use liquid parenteral formulation of tigecycline in vial.

In still further embodiments provided are ready-to-use liquid parenteral formulations including tigecycline and at least one or more pharmaceutically acceptable excipient or adjuvant in vial.

The storage-stable, ready-to-use, injectable compositions of the present application are useful as an antibiotic for a number of bacterial infections.

In one aspect, a liquid parenteral formulation is provided that include tigecycline and at least one or more pharmaceutically acceptable excipient or adjuvant, where the formulation is ready to use without additional steps for reconstitution at the time of administration.

In at least one embodiment, the formulation includes a pharmaceutically acceptable complex forming agent.

In at least one embodiment, the complex forming agent comprises at least one of calcium chloride and sodium chloride.

In at least one embodiment, the formulation includes a pharmaceutically acceptable antioxidant.

In at least one embodiment, the antioxidant comprises sodium bisulfite.

In at least one embodiment, after 62 days, the formulation total impurities do not exceed 1.13 and purity is at least 98.87.

In at least one embodiment, the tigecycline is charged into a sodium chloride solution.

In at least one embodiment, the tigecycline charged into a solution comprising a sodium chloride, calcium chloride, and sodium bisulfite.

In at least one embodiment, the formulation includes calcium chloride and sodium bisulfite.

In at least one embodiment, formulation purity is at least 98.17 after 24 days.

In at least one embodiment, the formulation includes a calcium chloride, sodium bisulfite, and a sodium chloride solution.

In at least one embodiment, purity of the formulation is at least 97.82 after 24 days.

In at least one embodiment, a pH of the formulation is adjusted from about 5.5 to about 6.5.

In at least one embodiment, the formulation is provided as a 100 ml, nitrogen flushed solution.

In at least one embodiment, the formulation is provided as a 5 ml, nitrogen flushed solution.

In at least one embodiment, tigecycline concentration of the formulation is from about 1 mg/ml to about 5 mg/ml.

In at least one embodiment, the formulation includes an amino acid.

In at least one embodiment, the amino acid comprises L-Histidine.

In at least one embodiment, the amino acid comprises L-Cysteine HCl.

In at least one embodiment, the amino acid L-Arginine.

DETAILED DESCRIPTION OF THE PREFERRED EMBODIMENTS

The details of one or more embodiments of the application are set forth in the description below. Other features, objects and advantages of the application will be apparent from the description.

The present application now will be described more fully hereinafter with reference to the accompanying examples and experiments, in which illustrative embodiments of the application are shown. This application may, however, be embodied in many different forms and should not be construed as limited to the embodiments set forth herein; rather, these embodiments are provided so that this disclosure will be thorough and complete, and will fully convey the scope of the application to those skilled in the art.

The terminology used herein is for the purpose of describing particular embodiments only and is not intended to be limiting of the application. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this application belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "tigecycline" refers to tigecycline and the pharmaceutically acceptable salts, solvates, hydrates and anhydrous forms thereof.

As used here in "ready-to-use" when used in connection with a tigecycline formulation refers to a formulation that includes tigecycline in dissolved or solubilized form and/or is intended to be used as such or upon further dilution in intravenous diluents.

As used herein, and unless otherwise specified, the term "storage-stable" refers to any tigecycline-containing composition or formulation having sufficient physical and chemical stability to allow storage at a convenient temperature, such as between about 0° C. and about 50° C., for a commercially reasonable period of time. The phrase "physical stability" refers to maintenance of colour or colourless state, dissolved oxygen level, head space oxygen level and particulate matter and the phrase "chemical stability" relates to formation of drug-related impurities in terms of total impurities, single maximum individual impurity, or maximum individual unknown impurity. For pharmaceutical products, stability is required for commercially relevant times after manufacturing, such as for about 6, 12, 18, 24, or 36 months, during which time a product is kept in its original packaging under specified storage conditions.

As used herein, and unless otherwise specified, the term "about" means an acceptable error for a particular value as determined by one of ordinary skill in the art, which depends in part on how the value is measured or determined. In certain embodiments, the term about means within 10%, 9%, 8%, 7%, 6%, 5%, 4%, 3%, 2%, 1%, 0.5%, 0.1%, or 0.05% of a given value or range.

In still further embodiments provided are ready-to-use liquid parenteral formulations including tigecycline and at least one or more pharmaceutically acceptable excipient or adjuvant.

In one or more further embodiment of present application pharmaceutically acceptable excipients or adjuvants include but are not limited to one or more preservatives, polymers, pH adjusting agents, isotonicity adjusting agents, surfactants, chelating agents and antioxidants.

Pharmaceutically acceptable excipients are not limited to complex forming agent, oxidizing agents and/or pH adjusting agents.

Pharmaceutically acceptable excipients or adjuvants include but are not limited to one or more preservatives, complex forming agents, pH adjusting agents, surfactants and antioxidants.

Examples of pharmaceutically acceptable preservatives include but are not limited to chlorobutanol, benzalkonium chloride, methyl paraben, propyl paraben, benzoic acid, sodium benzoate, sorbic acid, benzethonium chloride, cetyl pyridinium chloride, benzyl bromide, benzyl alcohol, phenylmercury nitrate, phenylmercury acetate, thiomersal, merthiolate, chlorhexidine, phenylethyl alcohol, quaternary ammonium chloride, sodium benzoate, etc. and combinations thereof.

Examples of pharmaceutically acceptable complex forming agents include but are not limited to sodium chloride, potassium chloride, calcium chloride and magnesium chloride, Arginine, glucose, glycerol, etc. and combinations thereof.

Examples of pharmaceutically acceptable antioxidants include but are not limited to butylated hydroxytoluene (BHT), butylated hydroxyanisole (BHA), sodium sulfite, Sodium bisulfite, propyl gallate (PG), monothioglycerol, ascorbic acid, sodium ascorbate, erythorbic acid, potassium metabisulfite, sodium metabisulfite, propionic acid, sodium formaldehyde sulphoxylate, reduced glutathione, thiourea, cysteine, n-aceticysteine, methionine, alkyl gallate, vitamin E or other tocopherol analogs such as tocopherol acetate and TPGS, etc. and combinations thereof.

Examples of pharmaceutically acceptable pH adjusting agents include but are not limited to sodium hydroxide, hydrochloric acid, meglumine, boric acid, citric acid, acetic acid, phosphoric acid, succinic acid, potassium hydroxide, ammonium hydroxide, magnesium oxide, calcium carbonate, magnesium carbonate, magnesium aluminum silicates, malic acid, potassium citrate, sodium phosphate, lactic acid, gluconic acid, tartaric acid, fumaric acid, diethanolamine, monoethanolamine, sodium carbonate, sodium bicarbonate, triethanolamine, etc. and combinations thereof.

The formulations according to the present application may be in the form of clear injectable solution, suspension or emulsion.

In some embodiments the storage-stable ready-to-use injectable formulation may have a concentration of tigecycline of less than 10 mg/ml. In other embodiments the injectable formulation may have a concentration of tigecycline of less than 7 mg/ml. In another embodiment the injectable formulation may have a concentration of tigecycline of less than 5 mg/ml. In other embodiments the injectable formulation may have a concentration of tigecycline of less than 3 mg/ml. In still other embodiments the concentration of tigecycline in the formulation may be about 1 mg/ml.

The storage-stable, ready-to-use injectable tigecycline-containing formulations disclosed herein do not require any additional reconstitution step(s) at the time of administration.

The formulations have a controlled impurity profile suitable for regulatory approval at various storage conditions. The storage-stable ready-to-use tigecycline formulations are stored at 2-8° C. The storage-stable, ready-to-use tigecycline formulations for injection may retain at least 94% of the potency of tigecycline after storage for six months at 2-8° C. temperature and 60% relative humidity.

The storage stable, ready-to-use, injectable formulations may be formulated to provide single or multiple dosage administration. The single dosage formulation may be packaged in IV bag, an ampoule, a vial, or a syringe. Multiple dosage formulations may be packaged in a vial. Multiple dosage formulations may preferably include at least one preservative.

The formulations have a pH value from about 3 to about 9. In some embodiments the pH range is from about 4 to about 8. In other embodiments the pH is about 5.5-6.5.

Storage-stable ready-to-use, injectable formulations disclosed herein contain tigecycline having a purity of from about 80% to about 120%. In some embodiments the formulation contains tigecycline having a purity of from about 90% to about 110%. In some embodiments the formulation contains tigecycline having a purity of about 100%.

Methods of treatment of such antibiotics are disclosed including administering to an individual in need thereof a therapeutically effective amount of a storage stable, ready-to-use, injectable formulation as disclosed herein.

Formulations as disclosed herein are useful as an antibiotic for skin and skin structure infections caused by susceptible isolates of *Escherichia coli*, *Enterococcus faecalis* (vancomycin-susceptible isolates), *Staphylococcus aureus* (methicillin-susceptible and -resistant isolates), *Streptococcus agalactiae*, *Streptococcus anginosus* grp. (includes *S. anginosus*, *S. intermedius*, and *S. constellatus*), *Streptococcus pyogenes*, *Enterobacter cloacae*, *Klebsiella pneumoniae*, and *Bacteroides fragilis*.

Prepared formulations are also used in patients 18 years of age and older for the treatment of complicated intra-abdominal infections caused by susceptible isolates of *Citrobacter freundii*, *Enterobacter cloacae*, *Escherichia coli*, *Klebsiella oxytoca*, *Klebsiella pneumoniae*, *Enterococcus faecalis* (vancomycin-susceptible isolates), *Staphylococcus aureus* (methicillinsusceptible and -resistant isolates), *Streptococcus anginosus* grp. (includes *S. anginosus*, *S. intermedius*, and *S. constellatus*), *Bacteroides fragilis*, *Bacteroides thetaiotaomicron*, *Bacteroides uniformis*, *Bacteroides vulgatus*, *Clostridium perfringens*, and *Peptostreptococcus micros*.

EXAMPLES

The following examples are for the illustration only and are not intended in any way to limit the scope of the present application.

Example 1

TABLE 1

| Ingredients | Qty/IV bag |
| --- | --- |
| Tigecycline | 100 mg |
| Calcium chloride | 60 mg |
| Sodium bisulfite | 2.5 mg |
| Sodium chloride | 900 mg |
| Sterile Water for Injection (WFI) | 100 ml |
| Meglumine (for pH adjustment) | q.s. |

In this example, 900 mg sodium chloride, 60 mg Calcium chloride and 2.5 mg Sodium bisulfite were dissolved in 45 ml of sterile water for injection. The pH of the solution was adjusted to 5.5-6.5 range using 0.1 M Meglumine solutions. The volume of the solution was made up to 100 ml with sterile water for injection. The solution was nitrogen purged until the dissolved oxygen reaches <0.1 mg/L level. The solution was divided into two parts—80 ml and 20 ml. 80 ml part was poured in an infusion bag (Solution A), 20 ml part was poured in plastic tube (Solution B).

Solution A and Solution B were then further nitrogen purged for another 30 minutes and closed tightly after nitrogen flushing and covered with black cover. Solution A and solution B were stored in refrigerator (2-8° C.) for 02 hours. 100 mg tigecycline was charged in solution B followed by the addition of solution B to solution A while the solution A was kept at ice bath (e.g., about 0° C.). Now, the total 100 ml solution in the infusion bag was nitrogen purged for another 15 minutes and sealed after nitrogen flushing and stored at refrigerator (2-8° C.).

Stability data is summarized in Table 1A. As can be seen, total impurities did not exceed 1.13 and purity was at least 98.88 after 62 days.

TABLE 1A

| | Stability | |
| --- | --- | --- |
| | Day 1 | Day 62 |
| Purity | 98.46 | 98.88 |
| Open Ring Tig. | ND | ND |
| Oxo Impurity | 0.09 | 0.03 |
| Rel. Comp. B | 0.13 | 0.05 |
| Epimer Impurity | 0.57 | 0.69 |
| Quinone Analogue | ND | 0.02 |
| Minocycline | ND | 0.02 |
| Tricyclic Impurity | 0.02 | 0.08 |
| Max. Unk Imp. | 0.25 | 0.06 |
| Total impurities | 1.44 | 1.13 |

Example 2

TABLE 2

| Ingredients | Qty/IV bag |
| --- | --- |
| Tigecycline | 100 mg |
| Calcium chloride | 60 mg |
| Sodium bisulfite | 2.5 mg |
| Sodium chloride | 900 mg |
| Sterile Water for Injection | 100 ml |

In this example, 900 mg sodium chloride, 60 mg Calcium chloride and 2.5 mg Sodium bisulfite were dissolved in 45 ml of sterile water for injection. The volume of the solution was made up to 100 ml with sterile water for injection. The solution was nitrogen purged until the dissolved oxygen reaches <0.1 mg/L level. The solution was divided into two parts—80 ml and 20 ml. 80 ml part was poured in an infusion bag (Solution A), 20 ml part was poured in plastic tube (Solution B).

Solution A and Solution B were then further nitrogen purged for another 30 minutes and closed tightly after nitrogen flushing and covered with black cover. Solution A and solution B were stored in refrigerator (2-8° C.) for 02 hours. 100 mg tigecycline was charged in solution B followed by the addition of solution B to solution A while the solution A was kept at ice bath (e.g., about 0° C.). Now, the total 100 ml solution in the infusion bag was nitrogen purged for another 15 minutes and sealed after nitrogen flushing and stored at refrigerator (2-8° C.). Stability data is summarized in Table 2A. As can be seen, total impurities did not exceed 1.13 and purity was at least 98.87 after 62 days.

total 100 ml solution in the infusion bag was nitrogen purged for another 15 minutes and sealed after nitrogen flushing and stored at RT and analysed on particular interval to check the stability. Stability data is summarized in Table 3A.

TABLE 3A

|  | API | Initial | 1 hr 10 min | 2 hr 20 min | 3 hr 30 min | 4 hr 40 min |
|---|---|---|---|---|---|---|
| % Purity | 99.22 | 99.11 | 99.14 | 99.14 | 99.11 | 99.11 |
| Open Ring Tig. | ND | ND | ND | ND | ND | ND |
| Oxo Impurity | 0.02 | 0.02 | 0.02 | 0.03 | 0.02 | 0.03 |
| Rel. Comp. B | 0.01 | 0.02 | 0.02 | 0.02 | 0.02 | 0.02 |
| Epimer Impurity | 0.5 | 0.53 | 0.54 | 0.55 | 0.56 | 0.56 |
| Quinone Analogue | ND | ND | ND | ND | ND | ND |
| Minocycline | ND | 0.04 | 0.04 | 0.04 | 0.04 | 0.04 |
| Tricyclic Impurity | 0.03 | 0.08 | 0.08 | 0.08 | 0.09 | 0.08 |
| Max. Unk Imp. | 0.05 | 0.05 | 0.05 | 0.05 | 0.05 | 0.05 |

| | Stability | |
|---|---|---|
| | Day 1 | Day 42 |
| Purity | 99.15 | 98.87 |
| Open Ring Tig. | ND | ND |
| Oxo Impurity | 0.03 | 0.21 |
| Rel. Comp. B | 0.02 | 0.05 |
| Epimer Impurity | 0.52 | 0.62 |
| Quinone Analogue | ND | 0.01 |
| Minocycline | ND | 0.03 |
| Tricyclic Impurity | 0.03 | 0.02 |
| Max. Unk Imp. | 0.05 | 0.04 |
| Total impurities | 0.85 | 1.13 |

Example 3 (Solution Stability at RT)

TABLE 3

| Ingredients | Qty/IV bag |
|---|---|
| Tigecycline | 100 mg |
| Calcium chloride | 60 mg |
| Sodium bisulfite | 2.5 mg |
| Sodium chloride | 900 mg |
| Sterile Water for Injection | 100 ml |
| Meglumine (for pH adjustment) | q.s. |

In this example, 900 mg sodium chloride, 60 mg Calcium chloride and 2.5 mg Sodium bisulfite were similarly dissolved in 45 ml of sterile water for injection. The pH of the solution was adjusted to 5.5-6.5 range using 0.1 M Meglumine solutions. The volume of the solution was made up to 100 ml with sterile water for injection. The solution was nitrogen purged until the dissolved oxygen reaches <0.1 mg/L level. The solution was divided into two parts 80 ml and 20 ml. 80 ml part was poured in the infusion bag (Solution A), 20 ml part was poured in plastic tube (Solution B).

Solution A and Solution B were then further nitrogen purged for another 30 minutes and closed tightly after nitrogen flushing and covered with black cover. Solution A and solution B were stored in refrigerator (2-8° C.) for 02 hours. 100 mg tigecycline was charged in solution B followed by the addition of solution B to solution A while the solution A was kept at ice bath (e.g., about 0° C.). Now, the Example 4

TABLE 4

| Ingredients | Qty/vial |
|---|---|
| Tigecycline | 50 mg |
| Calcium chloride | 60 mg |
| 5% Dextrose Solution | 5 ml |
| Sodium bisulfite | 2.5 mg |

Calcium chloride 60 mg and sodium bisulfite 2.5 mg were dissolved in 3 ml 5% dextrose for injection. The volume was made up to 5 ml with 5% dextrose solution. The solution was then nitrogen purged until dissolved oxygen reached <0.1 mg/L. 50 mg tigecycline was transferred into an amber color vial and then the 5 ml of the above solution was poured in the vial under nitrogen. The headspace of the vial was flushed through with nitrogen and packed. The vials were stored at refrigeration condition. Stability data is summarized in Table 4A.

TABLE 4A

| Stability | API | Day 24 |
|---|---|---|
| Purity | 99.3 | 98.17 |
| Open Ring Tig. | ND | ND |
| Oxo Impurity | 0.02 | 0.28 |
| Rel. Comp. B | 0.02 | 0.32 |
| Epimer Impurity | 0.48 | 0.82 |
| Quinone Analogue | ND | 0.03 |
| Minocycline | ND | ND |
| Tricyclic Impurity | 0.04 | 0.06 |
| Max. Unk Imp. | 0.05 | 0.05 |

Example 5

TABLE 5

| Ingredients | Qty/vial |
|---|---|
| Tigecycline | 50 mg |
| Calcium chloride | 60 mg |
| 5% Dextrose Solution | 5 ml |
| Sodium bisulfite | 2.5 mg |
| Meglumine (for pH adjustment) | q.s. |

Calcium chloride 60 mg and sodium bisulfite 2.5 mg were dissolved in 3 ml 5% dextrose. pH was adjusted to 5.5-6.0 pH range using 0.1 M meglumine solution, as required. The volume was made up to 5 ml with 5% dextrose solution. The solution was then nitrogen purged until dissolved oxygen reached <0.1 mg/L. 50 mg tigecycline was transferred into an amber colour vial and then the 5 ml of the above solution was poured in the vial under nitrogen. The headspace of the vial was flushed through with nitrogen and packed. The vials were stored at refrigeration condition. Stability data is summarized in Table 5A.

TABLE 5A

| Stability | API | Day 24 |
|---|---|---|
| Purity | 99.3 | 98.52 |
| Open Ring Tig. | ND | ND |
| Oxo Impurity | 0.02 | 0.13 |
| Rel. Comp. B | 0.02 | 0.24 |
| Epimer Impurity | 0.48 | 0.83 |
| Quinone Analogue | ND | 0.03 |
| Minocycline | ND | ND |
| Tricyclic Impurity | 0.04 | 0.06 |
| Max. Unk Imp. | 0.05 | 0.05 |

Example 6

TABLE 6

| Ingredients | Qty/vial |
|---|---|
| Tigecycline | 50 mg |
| Calcium chloride | 60 mg |
| 5% Dextrose Solution | 5 ml |
| Sodium bisulfite | 2.5 mg |
| Meglumine (for pH adjustment) | q.s. |

Calcium chloride 60 mg and sodium bisulfite 2.5 mg were dissolved in 3 ml 5% dextrose. pH was adjusted to 4.5-5.0 pH range using 0.1 M meglumine solution, as required. The volume was made up to 5 ml with 5% dextrose solution. The solution was then nitrogen purged until dissolved oxygen reached <0.1 mg/L. 50 mg tigecycline was transferred into an amber colour vial and then the 5 ml of the above solution was poured in the vial under nitrogen. The headspace of the vial was flushed through with nitrogen and packed. The vials were stored at refrigeration condition. Stability data is summarized in Table 6A.

TABLE 6A

| Stability | API | Day 24 |
|---|---|---|
| Purity | 99.3 | 98.24 |
| Open Ring Tig. | ND | ND |
| Oxo Impurity | 0.02 | 0.26 |
| Rel. Comp. B | 0.02 | 0.36 |
| Epimer Impurity | 0.48 | 0.81 |
| Quinone Analogue | ND | 0.03 |
| Minocycline | ND | ND |
| Tricyclic Impurity | 0.04 | 0.06 |
| Max. Unk Imp. | 0.05 | 0.05 |

Example 7

TABLE 7

| Ingredients | Qty/vial |
|---|---|
| Tigecycline | 50 mg |
| Calcium chloride | 60 mg |
| 0.9% NaCl Solution | 5 ml |
| Sodium bisulfite | 2.5 mg |

Calcium chloride 60 mg and sodium bisulfite 2.5 mg were dissolved in 3 ml 0.9% NaCl Solution. The volume was made up to 5 ml with 0.9% NaCl Solution. The solution was then nitrogen purged until dissolved oxygen reached <0.1 mg/L. 50 mg tigecycline was transferred into an amber color vial and then the 5 ml of the above solution was poured in the vial under nitrogen. The headspace of the vial was flushed through with nitrogen and packed. The vials were stored at refrigeration condition. Stability data is summarized in Table 7A.

TABLE 7A

| Stability | API | Day 64 |
|---|---|---|
| Purity | 99.3 | 97.82 |
| Open Ring Tig. | ND | ND |
| Oxo Impurity | 0.02 | 0.43 |
| Rel. Comp. B | 0.02 | 0.54 |
| Epimer Impurity | 0.48 | 0.97 |
| Quinone Analogue | ND | 0.02 |
| Minocycline | ND | ND |
| Tricyclic Impurity | 0.04 | 0.05 |
| Max. Unk Imp. | 0.05 | 0.16 |

Example 8

TABLE 8

| Ingredients | Qty/vial |
|---|---|
| Tigecycline | 50 mg |
| Calcium chloride | 60 mg |
| 0.9% NaCl Solution | 5 ml |
| Sodium bisulfite | 2.5 mg |
| Meglumine (for pH adjustment) | q.s. |

Calcium chloride 60 mg and sodium bisulfite 2.5 mg were dissolved in 3 ml 0.9% NaCl Solution. pH was adjusted to 5.5-6.0 pH range using 0.1 M meglumine solution, as required. The volume was made up to 5 ml with 0.9% NaCl Solution. The solution was then nitrogen purged until dissolved oxygen reached <0.1 mg/L. 50 mg tigecycline was transferred into an amber colour vial and then the 5 ml of the above solution was poured in the vial under nitrogen. The headspace of the vial was flushed through with nitrogen and packed. The vials were stored at refrigeration condition. Stability data is summarized in Table 8A.

TABLE 8A

| Stability | API | Day 64 |
|---|---|---|
| Purity | 99.3 | 98.03 |
| Open Ring Tig. | ND | ND |
| Oxo Impurity | 0.02 | 0.23 |

TABLE 8A-continued

| Stability | API | Day 64 |
|---|---|---|
| Rel. Comp. B | 0.02 | 0.5 |
| Epimer Impurity | 0.48 | 1.01 |
| Quinone Analogue | ND | 0.03 |
| Minocycline | ND | 0.03 |
| Tricyclic Impurity | 0.04 | 0.04 |
| Max. Unk Imp. | 0.05 | 0.14 |

Example 9

TABLE 9

| Ingredients | Qty/vial |
|---|---|
| Tigecycline | 50 mg |
| Calcium chloride | 60 mg |
| 0.9% NaCl Solution | 5 ml |
| Sodium bisulfite | 2.5 mg |
| Meglumine (for pH adjustment) | q.s. |

Calcium chloride 60 mg and sodium bisulfite 2.5 mg were dissolved in 3 ml 0.9% NaCl Solution. pH was adjusted to 4.5-5.0 pH range using 0.1 M meglumine solution, as required. The volume was made up to 5 ml with 0.9% NaCl Solution. The solution was then nitrogen purged until dissolved oxygen reached <0.1 mg/L. 50 mg tigecycline was transferred into an amber colour vial and then the 5 ml of the above solution was poured in the vial under nitrogen. The headspace of the vial was flushed through with nitrogen and packed. The vials were stored at refrigeration condition. Stability data is summarized in Table 9A.

TABLE 9A

| Stability | API | Day 24 |
|---|---|---|
| Purity | 99.3 | 98.5 |
| Open Ring Tig. | ND | ND |
| Oxo Impurity | 0.02 | 0.12 |
| Rel. Comp. B | 0.02 | 0.3 |
| Epimer Impurity | 0.48 | 0.78 |
| Quinone Analogue | ND | 0.04 |
| Minocycline | ND | ND |
| Tricyclic Impurity | 0.04 | 0.05 |
| Max. Unk Imp. | 0.05 | 0.04 |

Example 10

TABLE 10

| Ingredients | Qty/vial |
|---|---|
| Tigecycline | 50 mg |
| Calcium chloride | 60 mg |
| 0.9% NaCl Solution | 5 ml |
| Sodium bisulfite | 2.5 mg |
| pH | NA |
| Meglumine (for pH adjustment) | NA |
| Storage | Refg. |

Calcium chloride and sodium bisulfite were dissolved in 3 ml 0.9% NaCl Solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 10A.

TABLE 10A

| Stability | API | 42 days |
|---|---|---|
| % Purity | 99.2 | 98.37 |
| Open Ring Tig. | ND | ND |
| Oxo Impurity | 0.02 | 0.17 |
| Related Compound B | 0.01 | 0.41 |
| Epimer Impurity | 0.5 | 0.84 |
| Quinone Analogue | ND | 0.02 |
| Minocycline | ND | ND |
| Tricyclic Impurity | 0.03 | 0.04 |
| Max. Unk Imp. | 0.05 | 0.14 |

Example 11

TABLE 11

| Ingredients | Qty/vial |
|---|---|
| Tigecycline | 50 mg |
| Calcium chloride | 60 mg |
| 0.9% NaCl Solution | 5 ml |
| Sodium bisulfite | 2.5 mg |
| pH | 5.5-6.0 |
| Meglumine | q.s. |
| Storage | Refg. |

Calcium chloride and sodium bisulfite were dissolved in 3 ml 0.9% NaCl Solution. pH was adjusted to required pH 5.5-6.0 using 0.1 M meglumine solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 11A

TABLE 11A

| Stability | API | 42 days |
|---|---|---|
| % Purity | 99.2 | 98.47 |
| Open Ring Tig. | ND | ND |
| Oxo Impurity | 0.02 | 0.16 |
| Related Compound B | 0.01 | 0.31 |
| Epimer Impurity | 0.5 | 0.78 |
| Quinone Analogue | ND | 0.02 |
| Minocycline | ND | ND |
| Tricyclic Impurity | 0.03 | 0.04 |
| Max. Unk Imp. | 0.05 | 0.21 |

Example 12

TABLE 12

| Ingredients | Qty/vial |
| --- | --- |
| Tigecycline | 50 mg |
| Calcium chloride | 60 mg |
| 0.9% NaCl Solution | 5 ml |
| Sodium bisulfite | 2.5 mg |
| pH | 6.5-7.0 |
| Meglumine | q.s. |
| Storage | Refg. |

Calcium chloride and sodium bisulfite were dissolved in 3 ml 0.9% NaCl Solution. pH was adjusted to required pH 6.5-7.0 using 0.1 M meglumine solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 12A

TABLE 12A

| Stability | API | 29 days |
| --- | --- | --- |
| % Purity | 99.2 | 98.98 |
| Open Ring Tig. | ND | ND |
| Oxo Impurity | 0.02 | 0.01 |
| Related Compound B | 0.01 | 0.07 |
| Epimer Impurity | 0.5 | 0.66 |
| Quinone Analogue | ND | 0.03 |
| Minocycline | ND | ND |
| Tricyclic Impurity | 0.05 | 0.04 |

Example 13

TABLE 13

| Ingredients | Qty/vial |
| --- | --- |
| Tigecycline | 50 mg |
| Calcium chloride | 60 mg |
| 0.9% NaCl Solution | 5 ml |
| Sodium bisulfite | 5 mg |
| pH | NA |
| Meglumine | NA |
| Storage | Refg. |

Calcium chloride and sodium bisulfite were dissolved in 3 ml 0.9% NaCl Solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 13A.

TABLE 13A

| Stability | API | 29 days |
| --- | --- | --- |
| % Purity | 99.2 | 98.49 |
| Open Ring Tig. | ND | ND |
| Oxo Impurity | 0.02 | 0.11 |
| Related Compound B | 0.01 | 0.24 |
| Epimer Impurity | 0.5 | 0.85 |
| Quinone Analogue | ND | 0.03 |
| Minocycline | ND | 0.03 |

Example 14

TABLE 14

| Ingredients | Qty/vial |
| --- | --- |
| Tigecycline | 50 mg |
| Calcium chloride | 30 mg |
| 0.9% NaCl Solution | 05 ml |
| Sodium bisulfite | 2.5 mg |
| pH | No pH adjst. |
| Meglumine | NA |
| Storage | Refg. |

Calcium chloride and sodium bisulfite were dissolved in 3 ml 0.9% NaCl Solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 14A.

TABLE 14A

| Stability | API | 18 days |
| --- | --- | --- |
| % Purity | 99.22 | 98.49 |
| Open Ring Tig. | ND | ND |
| Oxo Impurity | 0.02 | 0.18 |
| Rel. Comp. B | 0.01 | 0.33 |
| Epimer Impurity | 0.5 | 0.74 |
| Quinone Analogue | ND | 0.02 |
| Minocycline | ND | 0.03 |
| Tricyclic Impurity | 0.03 | 0.02 |
| Max. Unk Imp. | 0.05 | 0.18 |

Example 15

TABLE 15

| Ingredients | Qty/vial |
| --- | --- |
| Tigecycline | 50 mg |
| Calcium chloride | 30 mg |
| 0.9% NaCl Solution | 05 ml |
| Sodium bisulfite | 2.5 mg |
| pH | 5.5-6.5 |
| Meglumine | pH adjst. |
| Storage | Refg. |

Calcium chloride and sodium bisulfite were dissolved in 3 ml 0.9% NaCl Solution. pH was adjusted to required pH 5.5-6.0 using 0.1 M meglumine solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 15A

TABLE 15A

| Stability | API | 18 days |
|---|---|---|
| % Purity | 99.22 | 98.77 |
| Open Ring Tig. | ND | ND |
| Oxo Impurity | 0.02 | 0.11 |
| Rel. Comp. B | 0.01 | 0.18 |
| Epimer Impurity | 0.5 | 0.7 |
| Quinone Analogue | ND | 0.03 |
| Minocycline | ND | 0.04 |
| Tricyclic Impurity | 0.03 | 0.02 |
| Max. Unk Imp. | 0.05 | 0.14 |

Example 16

TABLE 16

| Ingredients | Qty/vial |
|---|---|
| Tigecycline | 50 mg |
| Calcium chloride | 30 mg |
| 0.9% NaCl Solution | 05 ml |
| Sodium bisulfite | 1.25 mg |
| pH | No pH adjst. |
| Meglumine | NA |
| Storage | Refg. |

Calcium chloride and sodium bisulfite were dissolved in 3 ml 0.9% NaCl Solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 16A

TABLE 16A

| Stability | API | 02 days |
|---|---|---|
| % Purity | 99.22 | 99.07 |
| Open Ring Tig. | ND | ND |
| Oxo Impurity | 0.02 | 0.05 |
| Rel. Comp. B | 0.01 | 0.06 |
| Epimer Impurity | 0.5 | 0.55 |
| Quinone Analogue | ND | ND |
| Minocycline | ND | 0.04 |
| Tricyclic Impurity | 0.03 | 0.05 |
| Max. Unk Imp. | 0.05 | 0.05 |

Example 17

TABLE 17

| Ingredients | Qty/vial |
|---|---|
| Tigecycline | 50 mg |
| Calcium chloride | 30 mg |
| 0.9% NaCl Solution | 05 ml |
| Sodium bisulfite | 1.25 mg |
| pH | 5.5-6.0 |
| Meglumine | pH adjst. |
| Storage | Refg. |

Calcium chloride and sodium bisulfite were dissolved in 3 ml 0.9% NaCl Solution. pH was adjusted to required pH 5.5-6.0 using 0.1 M meglumine solution. The volume was made up to 5 ml with sterile water for injection. The solution was then cooled. Cooled solution was then nitrogen purged until dissolved oxygen reached <0.1 mg/L. 50 mg tigecycline was transferred into an amber colour vial and then the 5 ml of the above cooled solution was poured in the vial under nitrogen in cooling condition. The headspace of the vial was flushed through with nitrogen and packed. The vials were stored at refrigeration condition. Stability data is summarized in Table 17A

TABLE 17A

| Stability | API | 02 days |
|---|---|---|
| % Purity | 99.22 | 99.09 |
| Open Ring Tig. | ND | ND |
| Oxo Impurity | 0.02 | 0.04 |
| Rel. Comp. B | 0.01 | 0.06 |
| Epimer Impurity | 0.5 | 0.55 |
| Quinone Analogue | ND | ND |
| Minocycline | ND | 0.04 |
| Tricyclic Impurity | 0.03 | 0.05 |
| Max. Unk Imp. | 0.05 | 0.05 |

Example 18

TABLE 18

| Ingredients | Qty/IV bag |
|---|---|
| Tigecycline | 100 mg |
| Calcium chloride | 60 mg |
| Sodium bisulfite | 2.50 mg |
| Sodium chloride | 900 mg |
| L-Cysteine HCl | 30 mg |
| WFI | 100 ml |
| pH | 5.0-6.0 |
| NaOH (for pH adjustment) | q.s. |
| HCl (for pH adjustment) | q.s. |

900 mg sodium chloride, 60 mg Calcium chloride, 2.5 mg sodium bisulfite, 30 mg cysteine HCl were dissolved in 70 ml water. pH was adjusted to 5.0-6.0 using NaOH & HCl solution. The solution was then nitrogen purged for an hour while kept on cooling. 100 mg tigecycline was dissolved in 10 ml water (nitrogen purged) and added to the above solution. The volume was made up to 100 ml with nitrogen purged cold water. The solution was further nitrogen purged for 15 minutes and sealed under nitrogen in the infusion bag. The above bag was packed in Aluminium pouch under vacuum. The formulation was stored at 2-8° C. Stability data is summarized in Table 18A.

TABLE 18A

| Stability | Day 32 |
|---|---|
| % purity | 98.35 |
| Openring Tigecycline | 0.01 |
| Oxo Impurity | 0.03 |
| Rel. Comp. B | 0.33 |
| Epimer Impurity | 0.81 |
| Quinone Analogue | 0.01 |
| Minocycline | ND |
| Tricyclic Impurity | 0.05 |
| Max. Unk. impurity | 0.15 |
| Total Impurity | 1.65 |

Example 19

TABLE 19

| Ingredients | Qty/IV bag |
|---|---|
| Tigecycline | 100 mg |
| Calcium chloride | 60 mg |
| Sodium bisulfite | 2.50 mg |
| Sodium chloride | 900 mg |
| L-Histidine | 90 mg |
| WFI | 100 ml |
| pH | 5.0-6.0 |
| NaOH (for pH adjustment) | q.s. |
| HCl (for pH adjustment) | q.s. |

900 mg sodium chloride, 60 mg Calcium chloride, 2.5 mg sodium bisulfite, 90 mg L-Histidine were dissolved in 70 ml water. pH was adjusted to 5.0-6.0 using NaOH & HCl solution. The solution was then nitrogen purged for an hour while kept on cooling. 100 mg tigecycline was dissolved in 10 ml water (nitrogen purged) and added to the above solution. The volume was made up to 100 ml with nitrogen purged cold water. The solution was further nitrogen purged for 15 minutes and sealed under nitrogen in the infusion bag. The above bag was packed in Aluminium pouch under vacuum. The formulation was stored at 2-8° C. Stability data is summarized in Table 19A.

TABLE 19A

| Stability | Day 32 |
|---|---|
| % purity | 98.28 |
| Openring Tigecycline | ND |
| Oxo Impurity | 0.19 |
| Rel. Comp. B | 0.07 |
| Epimer Impurity | 0.81 |
| Quinone Analogue | 0.01 |
| Minocycline | 0.01 |
| Tricyclic Impurity | 0.01 |
| Max. Unk. impurity | 0.17 |
| Total Impurity | 1.72 |

Example 20

TABLE 20

| Ingredients | Qty/IV bag |
|---|---|
| Tigecycline | 100 mg |
| Calcium chloride | 60 mg |
| Sodium bisulfite | 2.50 mg |
| Sodium chloride | 900 mg |
| Methionine | 160 mg |
| WFI | 100 ml |
| pH | 5.0-6.0 |
| NaOH (for pH adjustment) | q.s. |
| HCl (for pH adjustment) | q.s. |

900 mg sodium chloride, 60 mg Calcium chloride, 2.5 mg sodium bisulfite, 90 mg methionine were dissolved in 70 ml water. pH was adjusted to 5.0-6.0 using NaOH & HCl solution. The solution was then nitrogen purged for an hour while kept of cooling. 100 mg tigecycline was dissolved in 10 ml water (nitrogen purged) and added to the above solution. The volume was made up to 100 ml with nitrogen purged cold water. The solution was further nitrogen purged for 15 minutes and sealed under nitrogen in the infusion bag. The above bag was packed in Aluminium pouch under vacuum. The formulation was stored at 2-8° C. Stability data is summarized in Table 20A.

TABLE 20A

| Stability | Day 69 |
|---|---|
| % purity | 97.71 |
| Openring Tigecycline | ND |
| Oxo Impurity | 0.02 |
| Rel. Comp. B | 0.05 |
| Epimer Impurity | 1.36 |
| Quinone Analogue | 0.01 |
| Minocycline | ND |
| Tricyclic Impurity | 0.02 |
| Max. Unk. impurity | 0.14 |
| Total Impurity | 2.29 |

Above example was kept in an accelerated stability study at various temperatures. Results for this study is summarized in Table no. 20B.

TABLE 20B

| | Condition | | | | |
|---|---|---|---|---|---|
| | API | 2-8° C. | 25° C. | 40° C. | 60° C. |
| | | | Days | | |
| | Day 1 | Day 69 | Day 7 | Day 7 | 60 hr |
| % purity | 99.18 | 97.71 | 96.28 | 91.98 | 74.88 |
| Openring Tigecycline | ND | ND | ND | ND | ND |
| Oxo Impurity | 0.02 | 0.02 | 0.01 | 0.01 | 0.02 |
| Rel. Comp. B | 0.02 | 0.05 | 0.07 | 0.08 | 0.13 |
| Epimer Impurity | 0.49 | 1.36 | 2.58 | 6.73 | 20.64 |
| Quinone Analogue | ND | 0.01 | 0.04 | 0.21 | 1.94 |
| Minocycline | ND | ND | 0.01 | 0.01 | 0.01 |
| Tricyclic Impurity | 0.05 | 0.02 | 0.04 | 0.11 | 0.6 |
| Max. Unk. impurity | 0.04 | 0.14 | 0.2 | 0.27 | 0.39 |
| Total Impurity | 0.82 | 2.29 | 3.72 | 8.02 | 25.12 |

Example 21

TABLE 21

| Ingredients | Qty/IV bag |
|---|---|
| Tigecycline | 50 mg |
| Calcium chloride | 75 mg |

TABLE 21-continued

| Ingredients | Qty/IV bag |
| --- | --- |
| Sodium chloride | 450 mg |
| Methionine | 40 mg |
| L-arginine | 175 mg |
| WFI | 50 ml |
| pH | 5.0-6.0 |
| NaOH (for pH adjustment) | q.s. |
| HCl (for pH adjustment) | q.s. |

450 mg Sodium chloride, 175 mg L-arginine, 75 mg calcium chloride dihydrate, 40 mg methionine were dissolved in 40 ml sterile water for injection. pH was then adjusted to 5.0-5.5 using NaOH and HCl solution and volume was made up to 50 ml with water. The solution was then nitrogen purged for an hour (dissolved oxygen level<0.1 mg/L), the solution was kept on cooling. 50 mg tigecycline was added to the above solution while the solution was kept on cooling and protected from light. The above solution was further nitrogen purged for 15 minutes and sealed under nitrogen in the infusion bag. The solution was then stored at 2-8° C. The solution in the infusion bag was further packed in Aluminium pouch under vacuum. Stability data is summarized in Table 21A.

TABLE 21A

| Stability | Day 31 |
| --- | --- |
| % purity | 98.4 |
| Openring Tigecycline | ND |
| Oxo Impurity | 0.02 |
| Rel. Comp. B | 0.02 |
| Epimer Impurity | 0.7 |
| Quinone Analogue | 0.03 |
| Minocycline | ND |
| Tricyclic Impurity | 0.1 |
| Max. Unk. impurity | 0.07 |

Example 22

TABLE 22

| Ingredients | Qty/IV bag |
| --- | --- |
| Tigecycline | 50 mg |
| Calcium chloride | 250 mg |
| Sodium chloride | 450 mg |
| Methionine | 40 mg |
| WFI | 50 ml |
| pH | 5.0-6.0 |
| NaOH (for pH adjustment) | q.s. |
| HCl (for pH adjustment) | q.s. |

450 mg Sodium chloride, 250 mg calcium chloride dihydrate, 40 mg methionine were dissolved in 40 ml sterile water for injection. pH was then adjusted to 5.0-5.5 using NaOH and HCl solution and volume was made up to 50 ml with water. The solution was then nitrogen purged for an hour (dissolved oxygen level<0.1 mg/L) while the solution was kept on cooling. 50 mg tigecycline was added to the above solution while the solution was kept on cooling and protected from light. The above solution was further nitrogen purged for 15 minutes and sealed under nitrogen in the infusion bag. The solution was then stored at 2-8° C. The solution in the infusion bag was further packed in Aluminium pouch under vacuum. Stability data is summarized in Table 22A.

TABLE 22A

| Stability | Day 31 |
| --- | --- |
| % purity | 98.67 |
| Openring Tigecycline | ND |
| Oxo Impurity | 0.02 |
| Rel. Comp. B | 0.02 |
| Epimer Impurity | 0.67 |
| Quinone Analogue | 0.01 |
| Minocycline | ND |
| Tricyclic Impurity | 0.06 |
| Max. Unk. impurity | 0.05 |

Example 23

TABLE 23

| Ingredients | Qty/IV bag |
| --- | --- |
| Tigecycline | 100 mg |
| Calcium chloride | 500 mg |
| Sodium chloride | 900 mg |
| Methionine | 80 mg |
| L-arginine | 350 mg |
| WFI | 100 ml |
| pH | 5.0-5.5 |
| NaOH (for pH adjustment) | q.s. |
| HCl (for pH adjustment) | q.s. |

900 mg Sodium chloride, 500 mg Calcium chloride dihydrate, 350 mg Arginine and 80 mg methionine were dissolved in 80 ml sterile water for injection. The pH was adjusted to 5.0 and the solution was nitrogen purged for an hour (dissolved oxygen level<0.1 mg/L) while the solution was kept on cooling. 100 mg tigecycline was added to and pH was adjusted to 5.2-5.3. The volume was made up to 100 ml with sterile water for injection. The sample was further nitrogen purged for 15 minutes while the solution was kept on cooling and protected from light and sealed under nitrogen in the infusion bag. The solution in the infusion bag was packed in Aluminium pouch under vacuum. The solution was then stored at 2-8° C. Stability data is summarized in Table 23A.

TABLE 23A

| Stability | Day 6 |
| --- | --- |
| % purity | 99.16 |
| Openring Tigecycline | ND |
| Oxo Impurity | 0.01 |
| Rel. Comp. B | 0.01 |
| Epimer Impurity | 0.46 |
| Quinone Analogue | ND |
| Minocycline | ND |
| Tricyclic Impurity | 0.07 |
| Max. Unk. impurity | 0.04 |

Example 24

TABLE 24

| Ingredients | Qty/IV bag |
| --- | --- |
| Tigecycline | 100 mg |
| Calcium chloride | 1000 mg |
| Sodium chloride | 900 mg |
| Methionine | 80 mg |

TABLE 24-continued

| Ingredients | Qty/IV bag |
|---|---|
| Arginine | 350 mg |
| WFI | 100 ml |
| pH | 5.0-5.5 |
| NaOH (for pH adjustment) | q.s. |
| HCl (for pH adjustment) | q.s. |

900 mg Sodium chloride, 1000 mg Calcium chloride dihydrate, 350 mg Arginine and 80 mg methionine were dissolved in 80 ml sterile water for injection. The pH was adjusted to 5.0 and the solution was nitrogen purged for an hour (dissolved oxygen level<0.1 mg/L) while the solution was kept on cooling. After purging 50 mg tigecycline was added and pH was adjusted to 5.2-5.3. The volume was made up to 100 ml with sterile water for injection. The sample was further nitrogen purged for 15 minutes while the solution was kept on cooling and protected from light and sealed under nitrogen in the infusion bag. The solution in the infusion bag was further packed in Aluminium pouch under vacuum. The solution was then stored at 2-8° C. Stability data is summarized in Table 24A.

TABLE 24A

| Stability | Day 7 |
|---|---|
| % purity | 98.88 |
| Openring Tigecycline | ND |
| Oxo Impurity | 0.03 |
| Rel. Comp. B | ND |
| Epimer Impurity | 0.52 |
| Quinone Analogue | ND |
| Minocycline | ND |
| Tricyclic Impurity | 0.05 |
| Max. Unk. impurity | 0.05 |

Example 25

TABLE 25

| Ingredients | Qty/IV bag |
|---|---|
| Tigecycline | 100 mg |
| Calcium chloride | 4000 mg |
| Sodium chloride | 900 mg |
| Methionine | 80 mg |
| Arginine | 350 mg |

TABLE 25-continued

| Ingredients | Qty/IV bag |
|---|---|
| WFI | 100 ml |
| pH | 5.0-5.5 |
| NaOH (for pH adjustment) | q.s. |
| HCl (for pH adjustment) | q.s. |

900 mg Sodium chloride, 4000 mg Calcium chloride dihydrate, 350 mg Arginine and 80 mg methionine were dissolved in 80 ml sterile water for injection. The pH was adjusted to 5.0-5.5 and the solution was nitrogen purged for an hour (dissolved oxygen level<0.1 mg/L) while the solution was kept on cooling. After purging 50 mg tigecycline was added and pH was adjusted to 5.2-5.3. The volume was made up to 100 ml with sterile water for injection. The sample was further nitrogen purged for 15 minutes while the solution was kept on cooling and protected from light and sealed under nitrogen in the infusion bag. The solution in the infusion bag was packed in Aluminium pouch under vacuum. The solution was then stored at 2-8° C. Stability data is summarized in Table 25A.

TABLE 25A

| Stability | Day 6 |
|---|---|
| % purity | 98.95 |
| Openring Tigecycline | ND |
| Oxo Impurity | 0.02 |
| Rel. Comp. B | 0.01 |
| Epimer Impurity | 0.52 |
| Quinone Analogue | ND |
| Minocycline | ND |
| Tricyclic Impurity | 0.05 |
| Max. Unk. impurity | 0.04 |

What is claimed is:

1. A liquid ready to use parenteral formulation, comprising tigecycline, calcium chloride, sodium chloride, sodium bisulfite, and optionally an amino acid selected from L-Histidine, L-Cysteine HCl or L-arginine; wherein concentration of tigecycline in the ready to use parenteral formulation is from 1 mg/ml to about 5 mg/ml and pH of the ready to use parenteral formulation is from 5.5 to 6.5.

2. The formulation of claim 1, provided as a 100 ml, nitrogen flushed solution.

3. The formulation of claim 1, provided as a 5 ml, nitrogen flushed solution.

\* \* \* \* \*